US00PP21565P2

(12) United States Plant Patent
Sanders

(10) Patent No.: US PP21,565 P2
(45) Date of Patent: Dec. 7, 2010

(54) ***AGERATUM* PLANT NAMED 'AGBAPUR'**

(50) Latin Name: *Ageratum houstonianum*
Varietal Denomination: Agbapur

(75) Inventor: Monica Maria Adelheid Sanders, Grootebroek (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/586,868

(22) Filed: Sep. 28, 2009

(51) Int. Cl.
*A01H 5/00* (2006.01)

(52) U.S. Cl. ..... Plt./400

(58) Field of Classification Search ..... Plt./263, Plt./400

See application file for complete search history.

*Primary Examiner*—Susan B McCormick Ewoldt
(74) *Attorney, Agent, or Firm*—S. Matthew Edwards

(57) ABSTRACT

A new *Ageratum* plant named 'Agbapur' particularly distinguished by its purple red flower color, early and continuous flowering, and its compact, upright, mounded and well branched growing habit.

1 Drawing Sheet

Latin name of the genus and species of the plant claimed: *Ageratum houstonianum.*

Varietal denomination: 'Agbapur'.

BACKGROUND OF THE NEW PLANT

The present invention comprises a new and distinct cultivar of *Ageratum,* botanically known as *Ageratum houstonianum.* The new cultivar is propagated from cuttings resulting from a cross between 'Y0017-3' as the female, or seed, parent and 'Y0039-3' as the male parent. This cross was made in September 2001. 'Y0017-3' is not commercially available and is not patented. 'Y0039-3' is not commercially available and is not patented.

The new *Ageratum* was discovered and selected as a single flowering plant within the progeny of the stated cross in 2004 in Enkhuizen, Netherlands. The new *Ageratum* has been repeatedly asexually reproduced by cuttings in Enkhuizen, Netherlands, in Gilroy, Calif., USA, in Angers, France, and in Sarrians, France since 2004. The distinctive characteristics of this new *Ageratum* are stable and reproduced true to type in successive generations of asexual reproduction. It takes 7 to 9 weeks to produce a finished plant, depending on the temperature.

This new *Ageratum* plant is an annual in most climatical zones in the US, only in zones 9 and 10 it is a perennial plant.

SUMMARY OF THE INVENTION

The following traits have been repeatedly observed and are determined to be the unique characteristics of 'Agbapur.' These characteristics in combination distinguish 'Agbapur' as a new and distinct *Ageratum* cultivar:

1. Compact, upright and mounded growth habit
2. Freely branching habit
3. Early and continuous flowering with many capitula in compound umbels
4. Large mid purple capitula on medium sized, green colored leaves

DESCRIPTION OF THE NEW CULTIVAR

The following detailed descriptions set forth the distinctive characteristics of this new *Ageratum.* The data which defines these characteristics were collected from asexual reproductions carried out in Enkhuizen, Netherlands. The plant history was taken on 28 week old plants, grown outdoors.

Color readings were taken in laboratory under ambient light. Color references are primarily to The R.H.S. Colour Chart of The Royal Horticultural Society of London.

TABLE 1

DIFFERENCES BETWEEN THE NEW CULTIVAR 'AGBAPUR' AND THE SIMILAR CULTIVAR 'AGMONTIS'

| | 'Agbapur' | 'Agmontis' (U.S. Plant Pat. No. 15,301) |
|---|---|---|
| Flower color: | Mid purple | Purple |
| Flower head: | Large | Medium |

Plants of the new *Ageratum* differ primarily from the plants of the female parent selection in the following characteristics:

Plants of the new *Ageratum* have a mid purple flower color, that does not bleach whereas plants of the female parent selection have a pale purple flower color.

Plants of the new *Ageratum* differ primarily from the male plant selection in the following characteristics:

Plants of the new *Ageratum* have a mid purple flower color whereas plants of the male parent selection have a light purple flower color.

Plants of the new *Ageratum* have a more vigerous growth whereas plants of the male parent selection have little growth.

DESCRIPTION OF THE DRAWING

This new *Ageratum* plant is illustrated by the accompanying photographic drawing which shows blooms, buds and foliage of the plant in full color, the color shown being as true as can be reasonably obtained by conventional photographic procedures.

The plant:

*Growth habit.*—Compact, upright, well branched.

*Plant height.*—18-21 cm.

*Spreading area of plant.*—36-42 cm.

*Growth rate.*—Compact.

*Strength.*—Very good.
*Branching character.*—Freely branching and lateral branching at every node.
*Blooming period.*—Year round.

The stem:
*Length.*—11-14 cm.
*Diameter.*—2 mm.
*Shape.*—Round.
*Color.*—RHS 141 C.
*Anthocyanin pigmentation.*—Absent.
*Length of internodes.*—19 mm.
*Texture.*—Slightly pubescent.

The foliage:
*Phyllotaxis.*—Alternate.
*Shape of blade.*—Ovate.
*Texture.*—Upper side: Slightly pubescent. Lower side: Slightly pubescent.
*Venation.*—Reticulate.
*Margin.*—Serrate.
*Base.*—Cordate.
*Apex.*—Acute.
*Length.*—23 mm.
*Width.*—21 mm.
*Color.*—Upper side: RHS 135A. Lower side: RHS 141A.
*Texture.*—Slightly pubescent.
*Petiole.*—Length: 5 mm. Diameter: 1 mm. Color: RHS 141C. Texture: Slightly pubescent.

The inflorescence:
*Type.*—Compound umbel of capitula.
*Number of inflorescences per plant.*—90-100.
*Umbel size.*—3.9 cm.
*Umbel depth.*—1.6 cm.
*Peduncle length.*—4 mm.
*Peduncle diameter.*—1.5 mm.
*Peduncle color.*—RHS 141B.
*Pedicel length.*—9 mm.
*Pedicel diameter.*—1 mm.
*Pedicel color.*—RHS 141C.
*Number of capitula per inflorescence.*—7.
*Number of disc florets per capitulum.*—85.
*Number of ray florets per capitulum.*—0.
*Disk floret.*—Corolla shape: Actinomorph. Number of lobes: 5 Length: 0.8 mm. Diameter: 1 mm. Color upper side: RHS N82A. Color lower side: RHS 155C.
*Phyllaries.*—Number per capitulum: 26. Length: 3 mm. Diameter: 0.8 mm. Color upperside: RHS 143A with tip RHS N79A. Color lower side: RHS 147C with tip RHS N79B.
*Capitulum.*—Shape in bud stage: Round, flat, showing unopened florets from the start. Depth: 4 mm. Diameter at beginning of flowering: 7 mm. Color at beginning of flowering: RHS N81A. Diameter at full flowering: 14 mm. Color at full flowering: RHS N88A.
*Fragrance.*—No fragrance.
*Lastingness of the bloom.*—Capitula of one umbel open over a period of 3 to 4 weeks.

Reproductive organs:
*Number of pistils.*—1.
*Pistil Shape.*—Style with two filiform branches.
*Length of stigma and style.*—6 mm.
*Stigma color.*—RHS N88A.
*Inferior ovary.*—5 ribbed.
*Pappus.*—Short.
*Number of anthers.*—5, connate in a tube, filaments free.
*Shape of anthers.*—Ecalcarate.
*Pollen quantity.*—A little pollen is present.
*Color of pollen.*—RHS 155B.

Seed development: Seed development has been observed on plants of the new *Ageratum.*
*Shape.*—Pentagonal.
*Length.*—2 mm.
*Diameter.*—0.8 mm.
*Color.*—RHS 202A.
*Pappus.*—Very short.

The roots:
*Root type.*—Fibrous.
*Root development.*—Roots develop on every part of the stem that contacts the soil.

Physiological and ecological characteristics: Plants of the new *Ageratum* are tolerant to temperatures between 4° C. and 35° C. Under commercial conditions, plants of the new *Ageratum* are strongly resistant to pests and diseases common to *Ageratum.*

What is claimed is:

1. A new and distinct variety of *Ageratum* plant named 'Agbapur,' as substantially illustrated and described herein.

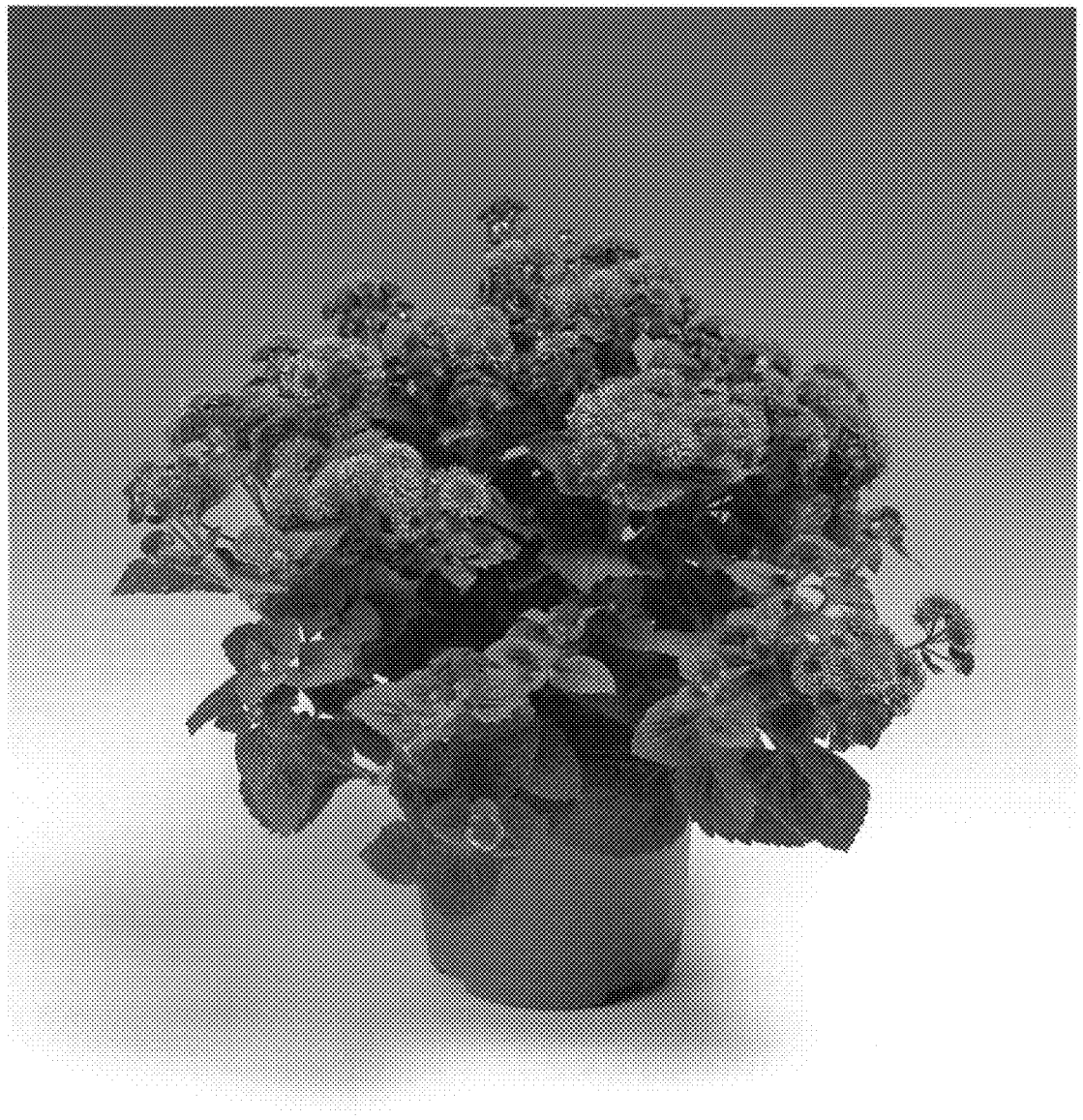

* * * * *